(12) United States Patent
Ogino et al.

(10) Patent No.: US 10,758,494 B2
(45) Date of Patent: *Sep. 1, 2020

(54) RIVASTIGMINE-CONTAINING ADHESIVE PATCH

(71) Applicant: KM TRANSDERM LTD., Osaka-shi, Osaka (JP)

(72) Inventors: Hiroyuki Ogino, Higashikagawa (JP); Masaoki Goto, Higashikagawa (JP); Atsuyo Hamada, Higashikagawa (JP); Mitsuji Akazawa, Higashikagawa (JP); Sadao Yukimoto, Higashikagawa (JP)

(73) Assignee: KM Transderm Ltd., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/406,691

(22) PCT Filed: Jun. 12, 2013

(86) PCT No.: PCT/JP2013/066273
§ 371 (c)(1),
(2) Date: Apr. 27, 2015

(87) PCT Pub. No.: WO2013/187451
PCT Pub. Date: Dec. 19, 2013

(65) Prior Publication Data
US 2015/0224063 A1    Aug. 13, 2015

(30) Foreign Application Priority Data

Jun. 12, 2012  (JP) ................ 2012-133268
Sep. 27, 2012  (JP) ................ 2012-230286
Sep. 27, 2012  (JP) ................ 2012-230287
Sep. 28, 2012  (JP) ................ 2012-230284
Sep. 28, 2012  (JP) ................ 2012-230285

(51) Int. Cl.
*A61K 9/70*       (2006.01)
*A61K 31/27*      (2006.01)
*A61K 31/325*     (2006.01)

(52) U.S. Cl.
CPC .......... *A61K 9/7038* (2013.01); *A61K 9/7053* (2013.01); *A61K 31/27* (2013.01); *A61K 31/325* (2013.01)

(58) Field of Classification Search
None
See application file for complete search history.

(56) References Cited

U.S. PATENT DOCUMENTS

| 6,583,220 | B1 * | 6/2003 | Lipman | C09J 153/02 525/54.3 |
| 6,689,379 | B1 | 2/2004 | Bracht | |
| 2001/0048938 | A1 | 12/2001 | Asmussen et al. | |
| 2003/0124179 | A1 | 7/2003 | Jacobsen et al. | |
| 2007/0128263 | A1 | 6/2007 | Gargiulo et al. | |
| 2012/0282303 | A1 | 11/2012 | Ito | |
| 2013/0220846 | A1 | 8/2013 | Hiraoka et al. | |
| 2013/0226112 | A1 * | 8/2013 | Akazawa | A61M 35/00 604/307 |

FOREIGN PATENT DOCUMENTS

| CN | 1354654 A | 6/2002 |
| CN | 101312717 A | 11/2008 |
| EP | 1284138 A1 | 2/2003 |
| EP | 2172194 A1 | 4/2010 |
| JP | H09-291028 A | 11/1997 |
| JP | H10-316559 A | 12/1998 |
| JP | 2001-302502 A | 10/2001 |
| JP | 2002-500178 A | 1/2002 |
| JP | 2002-542277 A | 12/2002 |
| JP | 2007-015963 A | 1/2007 |
| JP | 2009-517468 A | 4/2009 |
| JP | 2011-236379 A | 11/2011 |
| JP | 5093545 B1 | 9/2012 |
| KR | 10-2010-0080681 A | 7/2010 |
| WO | WO 1999/034782 A1 | 7/1999 |
| WO | WO 2000/012070 A1 | 3/2000 |
| WO | WO 2007/064407 A1 | 7/2007 |
| WO | WO2011/049038 * | 4/2011 |
| WO | WO2011/074635 * | 6/2011 |
| WO | WO 2011/074635 A1 | 7/2011 |
| WO | WO 2012/007150 A1 | 1/2012 |
| WO | WO 2012/029097 A1 | 3/2012 |
| WO | WO 2012/029325 * | 3/2012 |
| WO | WO 2012/029325 A1 | 3/2012 |
| WO | WO 2012/087047 A2 | 6/2012 |

OTHER PUBLICATIONS

WO2011/049038 Machine Transation, WIPO, accessed Feb. 25, 2016.* WO2011/074635, Machine Transation, WIPO, accessed Feb. 25, 2016.*
Wang et al., "Evaluation of Drug Release Profile from Patches Based on Styrene-Isoprene-Styrene Block Copolymer: The Effect of Block Structure and Plasticizer", AAPS PharmSciTech, 13(2), 2012, pp. 556-567. Published online Apr. 3, 2012.*
Roed-Petersen et al., "Contact dermatitis from antioxidants," *British Journal of Dermatology*, 94: 233-241 (1976).
Japan Patent Office, International Search Report in International Patent Application No. PCT/JP2013/066273 (dated Aug. 6, 2013).
European Patent Office, Supplementary European Search Report in European Patent Application No. 13803993 (dated Oct. 19, 2015).
Sonneborn, LLC, Sonneborn Refined Products: General Product Brochure, pp. 1-15 (2017).
The Japanese Ministry of Health, Labour and Welfare, *The Japanese Pharmacopoeia*, Seventeenth Edition, "Liquid Paraffin" and "Light Liquid Paraffin" entries, pp. 1365-1366 (2016).

* cited by examiner

*Primary Examiner* — Melissa L Fisher
(74) *Attorney, Agent, or Firm* — Leydig, Voit & Mayer, Ltd.

(57) ABSTRACT

The present invention provides a patch containing an adhesive layer maintaining a drug, which is formed on a support, wherein the aforementioned adhesive layer comprises a thermoplastic elastomer, a non-volatile hydrocarbon oil in an amount exceeding 50 parts by weight and not more than 800 parts by weight per 100 parts by weight of the elastomer, and rivastigmine or a salt thereof, and the aforementioned adhesive layer optionally further contains a tackifier at a content in the adhesive layer of not more than 10 wt %.

7 Claims, No Drawings

RIVASTIGMINE-CONTAINING ADHESIVE PATCH

CROSS-REFERENCE TO RELATED APPLICATIONS

This patent application is the U.S. national phase of International Patent Application No. PCT/JP2013/066273, filed Jun. 12, 2013, which claims the benefit of Japanese Patent Application No. 2012-133268, filed on Jun. 12, 2012, Japanese Patent Application No. 2012-230287, filed on Sep. 27, 2012, Japanese Patent Application No. 2012-230286, filed on Sep. 27, 2012, Japanese Patent Application No. 2012-230285, filed on Sep. 28, 2012, and Japanese Patent Application No. 2012-230284, filed on Sep. 28, 2012, which are incorporated by reference in their entireties herein.

TECHNICAL FIELD

The present invention relates to a patch containing rivastigmine. More particularly, the present invention relates to a patch which shows high skin permeability of rivastigmine, good transdermal absorbability and low skin irritation.

BACKGROUND ART

Alzheimer-type dementia is characterized in that nerve cell death, neurofibril changes and senile plaque formation occur in the cerebral cortex due to the deposition of extracellular β-amyloid, and atrophy of cerebral cortex, decreased glucose utilization by cerebrum, decreased perfusion in parietal lobe, lateral lobe cortex and prefrontal area cortex, and the like occur, as a result of which a progressive cognitive decline occurs. About 5% of the population aging 65 years or older are considered to be dementia patients, of which 40% is said to be of Alzheimer-type, which is the highest number of patients among the diseases accompanied by disappearance and degeneration of nerve cells, and this disease could be more and more serious in the ageing society in the future.

Therefore, it is difficult for patients with progressed Alzheimer-type dementia to live alone, and the disease lowers the quality of life (QOL) of patients themselves and patients' families taking care of them, and forces a large societal burden in terms of spiritual aspect and economical aspect.

The effect of rivastigmine, i.e., 3-[(1S)-1-(dimethylamino)ethyl]phenyl N-ethyl-N-methylcarbamate, on Alzheimer-type dementia is considered to be mainly attributable to the inhibition of acetylcholinesterase and butyrylcholinesterase, which increases intracerebral acetylcholine and activates the intracerebral cholinergic nerve system.

Recently, "EXELON PATCH", which is a patch of rivastigmine, has been placed in the market. This patch preparation has many advantages afforded by not being orally ingested, that side effects such as vomiting and the like can be suppressed, a rapid increase in the blood concentration can be suppressed and the like, since rivastigmine does not go into the stomach directly unlike oral drugs.

However, in the domestic clinical tests of EXELON PATCH, an adverse event such as skin reaction and stimulation at the application site was seen in 663 cases (77.3%) out of 858 cases as the safety analysis subjects, and the skin irritation at the application site poses a problem (non-patent document 1). In particular, many of the Alzheimer-type dementia patients are old. The skin of old person is prone to express skin symptoms more often, since it shows low moisturizing function, gets dry and highly likely shows low skin barrier function due to a decreased production quantity of sebum. When a patch showing skin irritation is adhered to such aged patients, the possibility is extremely high that some harmful phenomenon occurs on the skin.

As a patch containing rivastigmine, a transdermal absorption type preparation containing rivastiyiuine and an antioxidant in a matrix composed of polyacrylate or polymethacrylate (patent document 1), and a transdermal absorption type preparation containing a backing layer (support), a rivastigmine reservoir layer containing polyacrylate, polymethacrylate, polyisobutylene, polybutene, styrene-isoprene-styrene block copolymer and the like, and an adhesion layer containing a silicone polymer and a tackifier (patent document 2) are disclosed. However, the above-mentioned problem of skin irritation of a patch containing rivastigmine has entirely not been solved sufficiently.

On the other hand, as a transdermal absorption type preparation containing other drug, for example, a patch using a rubber-based, acrylate-based or silicone-based adhesion layer is disclosed as a patch of tolterodine, an antimuscarinic drug (patent document 3).

From the aspect of drug stability, moreover, a patch using a rubber-based adhesive showing less interaction with drugs has been proposed (patent documents 4-6).

DOCUMENT LIST

Patent Documents patent document 1: WO 99/034782
patent document 2: WO 2007/064407
patent document 3: WO 2000/12070
patent document 4: JP-A-2001-302502
patent document 5: JP-A-9-291028
patent document 6: JP-A-10-316559

Non-Patent Document non-patent document 1: pharmaceutical product interview form "EXELON PATCH" (rivastigmine transdermal absorption type preparation); revised in July 2011

SUMMARY OF THE INVENTION

Problems to be Solved by the Invention

The present inventors tried to develop a patch containing rivastigmine as a drug by using, for example, the adhesive layer components described in patent documents 3-6. However, it was clarified that a patch having a conventional adhesive layer containing a rubber-based adhesive and the like cannot ensure sufficient releaseability of rivastigmine. Also, it was clarified that the aforementioned patch generally requires addition of a tackifier to impart sufficient skin adhesiveness, and the tackifier causes skin irritation.

In view of the above-mentioned problems and the like, an object of the present invention is to provide a patch having sufficient skin adhesiveness and low skin irritation, showing good skin permeability of rivastigmine, and sufficient transdermal absorbability.

Means of Solving the Problems

The present inventors have conducted intensive studies in an attempt to solve the aforementioned problems and successfully reduced skin irritation while ensuring sufficient skin adhesiveness, by using, as components for forming an adhesive layer, a thermoplastic elastomer and a non-volatile hydrocarbon oil at a particular weight ratio relative to the elastomer, and reducing the content of tackifier. Furthermore, rivastigmine showed good skin permeability and sufficient transdermal absorbability, which resulted in the completion of the present invention.

Accordingly, the present invention relates to the following [1]-[13].

[1] A patch comprising an adhesive layer maintaining a drug, which is formed on a support,
wherein the aforementioned adhesive layer comprises
a thermoplastic elastomer,
a non-volatile hydrocarbon oil in an amount exceeding 50 parts by weight and not more than 800 parts by weight per 100 parts by weight of the elastomer, and
rivastigmine or a salt thereof, and
the aforementioned adhesive layer optionally further comprises a tackifier, and the content of the tackifier in the adhesive layer is not more than 10 wt %.
[2] The patch of the above-mentioned [1], wherein a content of the non-volatile hydrocarbon oil in the adhesive layer is not less than 23.5 wt % and not more than 88 wt %.
[3] The patch of the above-mentioned [1] or [2], wherein a content of the non-volatile hydrocarbon oil in the adhesive layer is more than 150 parts by weight and not more than 250 parts by weight per 100 parts by weight of the thermoplastic elastomer.
[4] The patch of any of the above-mentioned [1]-[3], wherein a content of the non-volatile hydrocarbon oil in the adhesive layer is not less than 50 wt % and not more than 70 wt %.
[5] The patch of any of the above-mentioned [1]-[4], wherein the non-volatile hydrocarbon oil is liquid paraffin.
[6] The patch of any of the above-mentioned [1]-[5], wherein the non-volatile hydrocarbon oil has kinematic viscosity at 40° C. of not less than 80 mm$^2$/s.
[7] The adhesive skin patch of any of the above-mentioned [1]-[6], wherein the thermoplastic elastomer is a styrene-based block copolymer.
[8] The patch of the above-mentioned [7], wherein the styrene-based block copolymer is a styrene-isoprene-styrene block copolymer.
[9] The patch of the above-mentioned [7], wherein the styrene-based block copolymer is a mixture of a styrene-isoprene-styrene block copolymer and a styrene-isoprene block copolymer.
[10] The patch of any of the above-mentioned [1]-[9], wherein the adhesive layer is free of a tackifier.
[11] The patch of any of the above-mentioned [1]-[10], wherein the adhesive layer is free of an antioxidant.
[12] A patch comprising a storage layer maintaining a drug and an adhesive layer, which are formed on a support,
wherein the aforementioned storage layer comprises rivastigmine or a salt thereof,
the aforementioned adhesive layer comprises
a thermoplastic elastomer, and
a non-volatile hydrocarbon oil in an amount exceeding 50 parts by weight and not more than 800 parts by weight per 100 parts by weight of the elastomer, and
rivastigmine or a salt thereof, and
the aforementioned adhesive layer optionally further comprises a tackifier, and the content of the tackifier in the adhesive layer is not more than 10 wt %.
[13] The patch of the above-mentioned [12], wherein a content of the non-volatile hydrocarbon oil in the adhesive layer is not less than 23.5 wt % and not more than 88 wt %.

Effect of the Invention

The patch of the present invention shows good skin permeability of rivastigmine and superior transdermal absorbability. Also, it has sufficient adhesiveness when adhered to the skin and causes low skin irritation.

DESCRIPTION OF EMBODIMENTS

The patch of the present invention (patch of first embodiment) comprises an adhesive layer maintaining a drug, which is formed on a support, wherein the aforementioned adhesive layer comprises a thermoplastic elastomer, a non-volatile hydrocarbon oil in an amount exceeding 50 parts by weight and not more than 800 parts by weight relative to 100 parts by weight of the elastomer, and rivastigmine or a salt thereof, and optionally comprises a tackifier at a content of not more than 10 wt % in the adhesive layer.

The patch of the present invention contains, in an adhesive layer, rivastigmine or a salt thereof as an active ingredient to be transdermally absorbed.

Specific examples of the salt of rivastigmine include acid addition salt of rivastigmine with organic acid such as monocarboxylic acid (acetic acid, propionic acid, butyric acid and the like); dicarboxylic acid (oxalic acid, malonic acid, fumaric acid, succinic acid, maleic acid and the like); hydroxycarboxylic acid (hydroxyacetic acid, lactic acid, malic acid, citric acid, tartaric acid and the like); carbonic acid; alkanesulfonic acid (methanesulfonic acid, ethanesulfonic acid and the like); amino acid (glutamic acid and the like) and the like, and acid addition salt with inorganic acid such as hydrochloric acid, hydrobromic acid, sulfuric acid, nitric acid, phosphoric acid and the like. Of these, rivastigmine tartrate is preferable from the aspects of easy availability, dispersibility in the adhesive layer and the like.

In the present invention, one or more kinds selected from the group consisting of the above-mentioned rivastigmine and salts thereof can be selected and used. From the aspects of dispersibility in the adhesive layer and transdermal absorbability, free (basic) rivastigmine is preferably used.

While the content of rivastigmine in the patch is not particularly limited, it is preferably 1 wt %-30 wt %, more preferably 2.5 wt %-25 wt %, most preferably 4 wt %-20 wt %, of the adhesive layer, in consideration of dispersibility in the adhesive layer and transdermal absorbability. In consideration of resistance of the patch to detachment in bathing and the like, it is preferably not more than 15 wt %.

The "thermoplastic elastomer" to be used in the present invention is an elastomer having thermoplasticity wherein it is softened when heat is added to show flowability, and returns to a rubbery elastic body by cooling, and various thermoplastic elastomers of urethane, acrylic, styrene, olefin series and the like can be mentioned. Particularly, styrene thermoplastic elastomer, especially styrene-based block copolymer, is preferably used to simultaneously achieve sufficient skin adhesiveness and low skin irritation, which is the object of the present invention.

Specific examples of the styrene-based block copolymer as a thermoplastic elastomer include styrene-butadiene block copolymer, styrene-butadiene-styrene block copolymer, styrene-isoprene block copolymer, styrene-isoprene-styrene block copolymer, styrene-ethylene/butylene block copolymer, styrene-ethylene/butylene-styrene block copolymer, styrene-ethylene/propylene block copolymer, styrene-ethylene/propylene-styrene block copolymer, styrene-isobutylene block copolymer, styrene-isobutylene-styrene block copolymer and the like. In the above, "ethylene/butylene"

shows an ethylene and butylene copolymer block, and "ethylene/propylene" shows an ethylene and propylene copolymer block. Only one kind of these styrene-based block copolymers may be used or two or more kinds thereof may be used in combination.

From the aspects of simultaneously achievement of sufficient skin adhesiveness and low skin irritation, and availability and handling property of the products for adhesive skin patch, of the above-mentioned styrene-based block copolymers, one or more kinds selected from the group consisting of a styrene-isoprene-styrene block copolymer and a styrene-isoprene block copolymer are preferably used. Particularly, a mixture of a styrene-isoprene-styrene block copolymer and a styrene-isoprene block copolymer is preferably used from the aspect of adhesiveness. When the mixing ratio of the styrene-isoprene block copolymer is too low, skin adhesiveness tends to decrease. When it is too high, shape retention of the adhesive layer tends to be degraded, which in turn may cause inconveniences on adhesion to the skin, such as adhesive residue on the skin after peeling off and the like. Therefore, the mixing ratio of the styrene-isoprene-styrene block copolymer and the styrene-isoprene block copolymer in weight ratio is preferably 10/90-82/18, more preferably 20/80-75/25, further preferably 30/70-70/30.

For the object of the present invention, a styrene-isoprene-styrene block copolymer preferably has a content of the styrene in the copolymer of 5 wt %-60 wt %, more preferably 10 wt %-50 wt %. In addition, it preferably has a weight average molecular weight as measured by gel filtration chromatography of 20,000-500,000, more preferably 30,000-300,000. As the styrene-isoprene block copolymer, one having a content of the styrene in the copolymer of 5 wt %-50 wt %, more preferably 10 wt %-40 wt %. In addition, it preferably has a weight average molecular weight as measured by gel filtration chromatography of 10,000-500,000, more preferably 20,000-300,000. The mixture of the styrene-isoprene-styrene block copolymer and the styrene-isoprene block copolymer preferably has a weight average molecular weight as measured by gel filtration chromatography of 20,000-500,000, more preferably 30,000-300,000.

As the styrene-isoprene-styrene block copolymer and the styrene-isoprene block copolymer, copolymers produced by a method known per se can be respectively used. As the styrene-isoprene-styrene block copolymer and the styrene-isoprene block copolymer, commercially available products that satisfy the above-mentioned properties can be respectively used. In addition, a mixture of the styrene-isoprene-styrene block copolymer and the styrene-isoprene block copolymer is also commercially available, and a commercially available product of a mixture of the styrene-isoprene-styrene block copolymer and the styrene-isoprene block copolymer at the above-mentioned mixing ratio, which satisfies the above-mentioned properties, can be preferably used.

Examples of the commercially available product include "KRATON D1161", "KRATON D1163", "KRATON D1113" and "KRATON D1119" manufactured by KRATON POLYMERS, "JSR SIS5229", "JSR SIS5403" and "JSR SIS5505" manufactured by JSR and the like.

When the content of the thermoplastic elastomer in the adhesive layer is too small, shape retention of the adhesive layer tends to be degraded. When it is too high, skin adhesiveness tends to be insufficient. Therefore, the content of the thermoplastic elastomer in the adhesive layer of the patch of the present invention is preferably not less than 8 wt %, more preferably not less than 10 wt %, still more preferably not less than 12 wt %, further preferably not less than 15 wt %, further more preferably not less than 18 wt %, particularly preferably not less than 20 wt %, particularly still more preferably not less than 24 wt %, most preferably not less than 28 wt %. It is preferably not more than 66 wt %, more preferably not more than 65 wt %, still more preferably not more than 64 wt %, further preferably not more than 49 wt %, further more preferably not more than 39 wt %.

In a more specifically preferable embodiment, the content of the thermoplastic elastomer in the adhesive layer is, for example, 8 wt %-66 wt %, more preferably 10 wt %-64 wt %, particularly preferably 12 wt %-49 wt %, most preferably 15 wt %-38 wt %.

In the patch of the present invention, the adhesive layer contains a non-volatile hydrocarbon oil.

As a non-volatile hydrocarbon oil, a chain saturated hydrocarbon having about 20-40 carbon atoms or a chain unsaturated hydrocarbon having about 20-40 carbon atoms is preferable and, for example, liquid paraffin, squalene, squalene, pristine and the like can be mentioned. In view of easy availability, liquid paraffin is more preferable. Liquid paraffin is a mixture of colorless odorless liquid alkane having not less than 20 carbon atoms. In the present invention, liquid paraffin compatible with the standard defined in the Japanese Pharmacopoeia, United States Pharmacopoeia and the like, and the like can be preferably used. The non-volatile hydrocarbon oil having high viscosity is preferable, and liquid paraffin having high viscosity is particularly preferably used from the aspect of adhesiveness.

To be specific, the non-volatile hydrocarbon oil preferably shows kinematic viscosity at 40° C. of not less than 60 $mm^2/s$, more preferably not less than 70 $mm^2/s$, particularly preferably not less than 80 $mm^2/s$. While the upper limit of the kinematic viscosity is not particularly limited, it is, for example, preferably not more than 500 $mm^2/s$, more preferably not more than 250 $mm^2/s$, from the aspects of easy handling, easy availability and the like.

The patch of the present invention contains the above-mentioned non-volatile hydrocarbon oil at a weight ratio of more than 50 parts by weight and not more than 800 parts by weight, relative to 100 parts by weight of the thermoplastic elastomer. When the content of the non-volatile hydrocarbon oil relative to 100 parts by weight of the thermoplastic elastomer is more than 800 parts by weight, shape retention of the adhesive layer becomes difficult. On the other hand, when the content of the non-volatile hydrocarbon oil is not more than 50 parts by weight, the adhesive becomes too hard and sufficient skin adhesiveness tends to be unachieved. Particularly, the followability to the moving skin during adhesion becomes poor, sometimes resulting in falling off during application. From such aspect, the content of the non-volatile hydrocarbon oil in the adhesive layer is preferably 51 parts by weight-800 parts by weight, more preferably 60 parts by weight-600 parts by weight, particularly preferably 70 parts by weight-500 parts by weight, relative to 100 parts by weight of the thermoplastic elastomer. Even in this range, when the content of the non-volatile hydrocarbon oil is high, peel stress from among the adhesiveness properties tends to decrease, protrusion of the adhesive is observed during preservation and adhesion, and inconveniences such as attachment to packing materials and clothes tend to occur. On the other hand, when the content of the non-volatile hydrocarbon oil is small, particularly, skin adhesiveness decreases during perspiration and bathing, and the patch may fall off. From such aspects, the content of the non-volatile hydrocarbon oil in the adhesive layer is preferably 80 parts by weight-400 parts by weight, more preferably 90 parts by weight-350 parts by weight, particularly preferably 100 parts by weight-300 parts by weight, relative to 100 parts by weight of the thermoplastic elastomer. Furthermore, when liquid paraffin having a kinematic viscosity at 40° C. of less than 80 mm$^2$/s is used as the non-volatile hydrocarbon oil, the content of the non-volatile hydrocarbon oil in the adhesive layer is preferably 150 parts by weight-250 parts by weight, more preferably 151 parts by weight-250 parts by weight, particularly preferably 153 parts by weight-248 parts by weight, most preferably 155 parts by weight-245 parts by weight, relative to 100 parts by weight of the thermoplastic elastomer.

The content of the non-volatile hydrocarbon oil in the adhesive layer is preferably not less than 23.5 wt %, more preferably not less than 25 wt %, still more preferably not less than 26.5 wt %, further preferably not less than 35 wt %, further more preferably not less than 45 wt %, and particularly preferably not less than 50 wt %. In addition, it is preferably not more than 88 wt %, more preferably not more than 85 wt %, still more preferably not more than 83 wt %, more preferably not more than 70 wt %, further more preferably not more than 68 wt %.

In a more specifically preferable embodiment, the content of the non-volatile hydrocarbon oil in the adhesive layer is, for example, 26.5 wt %-83 wt %, more preferably 35 wt %-80 wt %, particularly preferably 50 wt %-70 wt %.

In the present invention, it is preferable that the adhesive layer should contain no antioxidant to decrease skin irritation. The antioxidant here is added to prevent oxidative degradation of drugs. Examples thereof include tocopherol ester derivatives such as dibutylhydroxytoluene, ascorbic acid stearic acid ester, tocopherol, tocopherol acetate and the like, butylhydroxyanisole, 2-mercaptobenzimidazole, anthocyanin, catechin and the like.

In the patch of the present invention, the adhesive layer may further contain one or more kinds selected from the group consisting of alcohol solvents, amide solvents, ester solvents, liquid organic acids, carboxylic acid salts, lactone and surfactants to enhance dispersibility and transdermal absorbability of rivastigmine in the adhesive layer.

Examples of an alcohol solvent include higher saturated aliphatic alcohol having about 12-20 carbon atoms which is liquid at ambient temperature, such as lauryl alcohol, isostearyl alcohol, 2-octyldodecanol and the like; higher unsaturated aliphatic alcohol having about 12-20 carbon atoms which is liquid at ambient temperature, such as oleyl alcohol and the like; polyvalent alcohol which is liquid at ambient temperature such as ethylene glycol, propylene glycol, glycerol, 1,3-butanediol, polyethylene glycol having a molecular weight of about 100-600 and the like; and the like. The "ambient temperature" in the present specification is within the range of 15-25° C. in the principles of the Japanese Pharmacopoeia.

Of these, polyvalent alcohol which is liquid at ambient temperature such as ethylene glycol, propylene glycol, glycerol, 1,3-butanediol, polyethylene glycol and the like is preferable, diol which is liquid at ambient temperature such as ethylene glycol, propylene glycol, 1,3-butanediol, polyethylene glycol having a molecular weight of about 100-600 and the like are more preferable to improve the solubility of rivastigmine.

Examples of the amide solvent include pyrrolidones such as N-methyl-2-pyrrolidone, 2-pyrrolidone and the like; imidazolidinones such as 1,3-dimethyl-2-imidazolidinone and the like; N-substituted toluidines such as crotamiton and the like; alkaneamides such as formamide, N-methylformamide, N,N-dimethylformamide, N-methylacetamide, N,N-dimethylacetamide, N-methylpropaneamide and the like, and the like.

Among the above-mentioned amide solvents, N-methyl-2-pyrrolidone, crotamiton, N,N-dimethylformamide and N,N-dimethylacetamide are preferable, and N-methyl-2-pyrrolidone and crotamiton are more preferable, to improve solubility, dispersibility and transdermal absorbability of rivastigmine.

Examples of an ester solvent include ester of long chain fatty acid and monovalent aliphatic alcohol, medium-chain triglyceride, ester of polyvalent carboxylic acid and monovalent aliphatic alcohol, carbonate and the like.

As an ester of long chain fatty acid and monovalent aliphatic alcohol, an ester, which is liquid at ambient temperature, of long chain saturated fatty acid having 12-20 carbon atoms and monovalent aliphatic alcohol having 1-20 carbon atoms is preferable, and examples thereof include myristate which is liquid at ambient temperature such as ethyl myristate, isopropyl myristate, octyldodecyl myristate and the like, palmitate which is liquid at ambient temperature such as ethyl palmitate, isopropyl palmitate, isostearyl palmitate and the like, stearate which is liquid at ambient temperature such as isopropyl stearate and the like, and the like. In addition, an ester of long-chain unsaturated fatty acid having 12-20 carbon atoms and monovalent aliphatic alcohol having 1-20 carbon atoms can also be used preferably, and examples thereof include oleate which is liquid at ambient temperature such as ethyl oleate, decyl oleate, oleyl oleate and the like, linoleate which is liquid at ambient temperature such as ethyl linoleate, isopropyl linoleate and the like, and the like.

Medium-chain triglyceride is a triglyceride of fatty acid having about 6-12 carbon atoms such as caproic acid, caprylic acid, capric acid, lauric acid and the like, and glycerol. In the present invention, caprylic acid triglyceride, a triglyceride mixture of caprylic acid and capric acid, a triglyceride mixture of caprylic acid, capric acid and lauric acid, and the like, which are liquid at ambient temperature, can be used. In addition, fats and oils containing a large amount of these, which are liquid at ambient temperature, can also be used. Examples of such fats and oils include peanuts oil, olive oil, castor oil and the like.

As medium-chain triglyceride which is liquid at ambient temperature or medium-chain triglyceride containing fats and oils, which is liquid at ambient temperature, in the present invention, a commercially available product for pharmaceutical use can also be used.

Examples of the ester of polyvalent carboxylic acid and monovalent aliphatic alcohol include diester, which is liquid at ambient temperature, of dicarboxylic acid having 2-12 carbon atoms and monovalent aliphatic alcohol having 1-20 carbon atoms such as adipic acid diester which is liquid at ambient temperature such as diethyl adipate, diisopropyl adipate and the like, sebacic acid diester which is liquid at ambient temperature such as diethyl sebacate, diisopropyl sebacate, dioctyldodecyl sebacate and the like, and the like.

Examples of carbonate include cyclic carbonate of carbonic acid and diol having 2-10 carbon atoms, such as ethylene carbonate, propylene carbonate, vinylene carbonate and the like, with preference given to propylene carbonate.

Of the above-mentioned ester solvents, myristate, a medium-chain triglyceride mixture, sebacic acid diester and carbonate are preferable, isopropyl myristate, a triglyceride mixture of caprylic acid and capric acid, diethyl sebacate and propylene carbonate are more preferable.

In the present invention, one or more kinds of the above-mentioned alcohol solvents, amide solvents and ester solvents can be selected and used as necessary. The content of these solvents is preferably 0.1 wt %-20 wt %, more preferably 0.5 wt %-15 wt %, relative to the total amount of the adhesive layer.

Examples of the liquid organic acid include aliphatic monocarboxylic acids such as acetic acid, propionic acid, butyric acid, valeric acid, isovaleric acid, caproic acid, enanthic acid (heptanoic acid), caprylic acid, pelargric acid (nonanoic acid) and the like; aliphatic unsaturated monocarboxylic acids such as oleic acid, linoleic acid, arachidonic acid, docosahexaenoic acid and the like; hydroxycarboxylic acids such as lactic acid (DL-lactic acid, a mixture of L-lactic acid and/or D-lactic acid and anhydrous lactic acid) and the like; liquid carboxylic acids substituted by an alkoxy group such as methoxyacetic acid and the like; sulfonic acids such as methanesulfonic acid and the like, and the like.

These liquid organic acids have a function to aid dissolution of rivastigmine. As a result, rivastigmine with low solubility can be contained at a high concentration in the adhesive layer, dispersibility can also be improved, and further, transdermal absorbability can be improved. From such aspects, of these liquid organic acids, the Japanese Pharmacopoeia lactic acid and oleic acid are preferably used, and the Japanese Pharmacopoeia lactic acid is particularly preferably used.

In the present invention, one or more kinds selected from the above-mentioned liquid organic acids can be selected and contained as necessary. The content of the liquid organic acid is preferably 0.1 wt %-20 wt %, more preferably 0.5 wt %-15 wt %, relative to the total amount of the adhesive layer.

Examples of the carboxylic acid salt include salts of aliphatic monocarboxylic acid, alicyclic monocarboxylic acid, aliphatic dicarboxylic acid and the like.

Examples of aliphatic monocarboxylic acid include short chain fatty acids having 2-7 carbon atoms such as acetic acid, butyric acid, hexanoic acid and the like, middle chain fatty acids having 8-11 carbon atoms such as octanoic acid, decanoic acid and the like, long chain fatty acids having 12 or more carbon atoms such as myristic acid, stearic acid, isostearic acid, oleic acid and the like, hydroxymonocarboxylic acids such as glycolic acid, lactic acid, 3-hydroxybutyric acid, mandelic acid and the like, alkoxy group-substituted monocarboxylic acids such as methoxyacetic acid and the like, ketomonocarboxylic acids such as levulinic acid and the like, and the like.

Examples of alicyclic monocarboxylic acid include alicyclic monocarboxylic acids having 6-8 carbon atoms such as cyclohexane carboxylic acid and the like.

Examples of aliphatic dicarboxylic acid include sebacic acid, adipic acid, malic acid, maleic acid, fumaric acid and the like.

Preferable examples of carboxylic acid include long chain fatty acid having 12 or more carbon atoms and hydroxymonocarboxylic acid, such as myristic acid, stearic acid, isostearic acid, oleic acid and lactic acid. More preferred are oleic acid and lactic acid.

Examples of the salt of the above-mentioned carboxylic acid include alkali metal salts such as sodium salt, potassium salt and the like, alkaline earth metal salts such as calcium salt and the like, and amine salt. From the aspects of easy availability, and the effect of improving stability and transdermal absorbability, sodium salt is preferably used.

Examples of lactone include 5-membered ring lactones such as ascorbic acid, isoascorbic acid and the like, and the like.

In the patch of the present invention, sodium oleate, sodium lactate, ascorbic acid or isoascorbic acid is preferably used as carboxylic acid salt or lactone, in consideration of the effects of improving stability and transdermal absorbability of drugs.

When carboxylic acid salt or lactone is contained in the patch of the present invention, the content thereof in the adhesive layer is not particularly limited. However, it is preferably not less than 0.1 mol and not more than 5 mol, more preferably not less than 0.2 mol and not more than 3 mol, relative to 1 mol of rivastigmine. When the amount to be added is less than 0.1 mol relative to 1 mol of rivastigmine, a sufficient transdermal absorbability improving effect sometimes cannot be achieved. When the amount to be added is more than 5 mol relative to 1 mol of rivastigmine, the properties of preparation such as adhesive property and the like are sometimes degraded.

Examples of the surfactant include non-ionic surfactants such as polyoxyethylene fatty acid esters such as polyoxyethylene monolaurate and the like, polyoxyethylene sorbit fatty acid esters such as polyoxyethylene sorbit tetraoleate and the like, polyoxyethylene sorbitan ester of fatty acids such as polyoxyethylene sorbitan monooleate, polyoxyethylene sorbitan monolaurate, polyoxyethylene sorbitan monopalmitate and the like, sorbitan ester of fatty acids such as sorbitan monolaurate, sorbitan monooleate, sorbitan sesquioleate, sorbitan trioleate and the like, fatty acid esters of glycerol such as glycerol monooleate, polyoxyethylene castor oil derivative, polyoxyethylene hydrogenated castor oil and the like, polyoxyethylene higher aliphatic alcohol ethers such as polyoxyethylene lauryl ether, polyoxyethylene oleyl ether and the like, polyoxyethylene alkyl phenyl ethers such as polyoxyethylene nonyl phenyl ether and the like, polyoxyethylene polyoxypropylene copolymer such as pluronic L-31, pluronic L-44 and the like, and the like, anionic surfactants such as sodium alkylsulfates (e.g., sodium lauryl sulfate and the like) and the like, cationic surfactants such as alkyl trimethyl ammonium salt, alkyl dimethyl ammonium salt and the like, amphoteric surfactants such as alkyl dimethyl amine oxide, alkylcarboxybetaine and the like. One or more kinds selected therefrom can be used.

Of the above-mentioned surfactants, to enhance the transdermal absorbability, a non-ionic surfactant which is liquid at ambient temperature is preferable, sorbitan ester of fatty acid which is liquid at ambient temperature is more preferably, and sorbitan monolaurate is particularly preferable.

In the patch of the present invention, the content of a surfactant in the adhesive layer when it is contained is preferably 0.01 wt %-10 wt %, more preferably 0.1 wt %-5 wt %.

The patch of the present invention can exhibit good skin adhesiveness by containing a thermoplastic elastomer and a non-volatile hydrocarbon oil at the above-mentioned contents and content ratio to form an adhesive layer, and the adhesive layer may contain a tackifier as necessary.

Here, the tackifier is a resin widely used for conferring skin adhesiveness generally in the field of adhesive skin patch, and examples thereof include rosin resin, polyterpene resin, coumarone-indene resin, petroleum resin, terpene-phenol resin, alicyclic saturated hydrocarbon resin and the like. One or more kinds selected therefrom can be used.

However, when a tackifier is contained in the adhesive layer, the content of the tackifier in the adhesive layer is not more than 10 wt % to decrease skin irritation and the like. The content is preferably not more than 5 wt %, more preferably not more than 2 wt %, further preferably not more than 1 wt %, and the absence of a tackifier is most preferable.

That is, in relation to the skin adhesiveness of the patch, the content of the tackifier is adjusted according to the kind, content and content ratio of the thermoplastic elastomer and non-volatile hydrocarbon oil. When sufficient skin adhesiveness is obtained without containing a tackifier, a tackifier is not necessary.

The adhesive layer forming the patch of the present invention may contain, as optional components, pharmaceutically conventional additives such as excipient, dispersing agent, stabilizer, viscous agent, softening agent, flavoring agent, colorant and the like, as long as the characteristics of the present invention are not impaired.

Examples of the excipient to be used in the present invention include silicon compound such as silicic anhydride, light anhydrous silicic acid, silicic hydride and the like; cellulose derivative such as ethylcellulose, methylcellulose, hydroxypropylcellulose, hydroxypropylmethylcellulose and the like; water-soluble synthesis polymer such as polyvinyl alcohol and the like; aluminum compound such as dried aluminum hydroxide gel, water-containing aluminum silicate and the like; pigment such as kaolin, titanium oxide and the like; and the like.

In the present invention, one or more kinds selected from the above can be used as necessary.

Examples of the dispersing agent to be used in the present invention include gum arabic, propylene glycol alginate, sodium dioctyl sulfosuccinate, lecithin and the like.

In the present invention, one or more kinds selected from the above can be used as necessary.

Examples of the stabilizer to be used in the present invention include zinc stearate, gelatin, dextran, povidone and the like.

In the present invention, one or more kinds selected from the above can be used as necessary.

Examples of the viscous agent to be used in the present invention include carboxyvinyl polymer, xanthan gum, tragacanth, locust bean gum and the like.

In the present invention, one or more kinds selected from the above can be used as necessary.

Examples of the softening agent to be used in the present invention include fats and oils such as almond oil, rape seed oil, cottonseed oil-soybean oil mixture, process oil, beef tallow and the like; waxes such as purified lanolin and the like; esters which are solid at ambient temperature such as cetyl lactate and the like; rubbers such as polyisoprene rubber, polybutene, crude rubber and the like; polymer such as crystalline cellulose and the like; allantoin and the like.

In the present invention, one or more kinds selected from the above can be used as necessary.

Examples of the flavoring agent to be used in the present invention include d-camphor, dl-camphor, d-borneol, dl-borneol, cinnamaldehyde, peppermint oil, dl-menthol, l-menthol and the like.

In the present invention, one or more kinds selected from the above can be used as necessary.

Examples of the colorant to be used in the present invention include red ferric oxide, yellow iron oxide, yellow ferric oxide, carbon black and the like.

In the present invention, one or more kinds selected from the above can be used as necessary.

The adhesive skin patch of the present invention is prepared by casting an adhesive layer having the above-mentioned constitution on a support.

In the present invention, the "support" is not particularly limited, and one widely used for adhesive skin patches can be used. For example, stretchable or non-stretchable woven fabric or non-woven fabric of polyethylene, polypropylene and the like, a film of polyethylene, polypropylene, polyester such as poly(ethylene terephthalate) and the like, ethylene vinyl acetate copolymer, vinyl chloride and the like, or a foamed support of urethane, polyurethane and the like can be mentioned. These may be used singly or a laminate of plural kinds may be used. Furthermore, to prevent accumulation of static electricity on the support, an antistatic agent may be added to the aforementioned woven fabric, non-woven fabric, film and the like constituting the support. Also, to provide good anchor property to the adhesive layer, non-woven fabric, woven fabric or a laminate thereof with a film can be used as a support. The thickness of a film as the support is generally 10 μm-100 μm, preferably 15 μm-50 μm, and the thickness of woven fabric, non-woven fabric, and a porous sheet such as foamed support and the like is generally 50 μm-2,000 μm, preferably 100 μm-1,000 μm.

In addition, the adhesive skin patch of the present invention can also be provided with a release liner generally used in the field of adhesive skin patches. As the release liner, polyester such as glassine, polyethylene, polypropylene, poly(ethylene terephthalate) and the like, resin films such as polystyrene and the like, aluminum film, foamed polyethylene film, foamed polypropylene film and the like, or a laminate of two or more kinds of those mentioned above can be used. Moreover, these after silicone processing, fluorine resin processing, emboss processing, hydrophilic processing, hydrophobic processing and the like, and the like can also be used. The thickness of the release liner is generally 10 μm-200 μm, preferably 15 μm-150 μm.

The patch of the present invention can be produced, for example, by dissolving each of a thermoplastic elastomer and rivastigmine or a salt thereof in non-volatile hydrocarbon oil, dissolving or dispersing same in a solvent such as toluene and the like to prepare a coating liquid for forming an adhesive layer, applying the obtained coating liquid on a support, and then drying same. When a release liner is used, a release liner can be laminated by pressing same on an adhesive layer. Alternatively, the aforementioned solution is applied on a release liner, dried to form an adhesive layer on the surface of the release liner, and a support may be adhered by pressing same against the adhesive layer. A coating liquid for forming an adhesive layer can be applied using, for example, a conventionally-used coater such as roll coater, die coater, gravure roll coater, reverse roll coater, kiss-roll coater, dip roll coater, bar coater, knife coater, spray coater and the like. In addition, the aforementioned solution is preferably dried under heating at, for example, about 40° C.-150° C. The adhesive layer after drying, which contains rivastigmine is preferably 10 g/m$^2$-1,000 g/m$^2$, more preferably 20 g/m$^2$-800 g/m$^2$.

The patch of the present invention may be a patch in a form wherein a storage layer retaining a drug and an adhesive layer are formed on a support instead of an adhesive layer retaining a drug (patch of second embodiment).

In such patch, the storage layer retaining the drug (hereinafter to be also abbreviated as "drug storage layer") contains rivastigmine or a salt thereof, and the adhesive layer contains a thermoplastic elastomer and more than 50 parts by weight and not more than 800 parts by weight of a non-volatile hydrocarbon oil relative to 100 parts by weight of the elastomer. The adhesive layer may contain a tackifier, and the content of the tackifier in the adhesive layer is not more than 10 wt %.

The components constituting the drug storage layer are not particularly limited and, for example, the components described in patent document 2 can be mentioned. The "thermoplastic elastomer" and "non-volatile hydrocarbon oil" to be used in the adhesive layer can be used as the constituent components of the drug storage layer.

Specific examples of the salt of rivastigmine are the same as those exemplified for the patch of the aforementioned first embodiment. From the aspects of dispersibility in the drug storage layer and transdermal absorbability, free (basic) rivastigmine is preferably used.

While the content of the drug in the patch is not particularly limited, it is preferably 1 wt %-30 wt %, more preferably 2.5 wt %-25 wt %, most preferably 4 wt %-20 wt %, of the drug storage layer, in consideration of the dispersibility in the drug storage layer and transdermal absorbability.

The "thermoplastic elastomer" to be used in the adhesive layer is the same as the "thermoplastic elastomer" of the "adhesive layer maintaining the drug" of the patch of the aforementioned first embodiment, and preferable embodiments thereof are also the same. The content of the thermoplastic elastomer in the adhesive layer is preferably 8 wt %-66 wt %, more preferably 10 wt %-65 wt %, particularly preferably 12 wt %-64 wt %.

The "non-volatile hydrocarbon oil" contained in the adhesive layer is the same as the "non-volatile hydrocarbon oil" of the "adhesive layer maintaining the drug" of the patch of the aforementioned first embodiment, and preferable embodiments thereof are also the same. The adhesive layer contains a non-volatile hydrocarbon oil at a weight ratio of more than 50 parts by weight and not more than 800 parts by weight relative to 100 parts by weight of the thermoplastic elastomer. When the content of the non-volatile hydrocarbon oil relative to 100 parts by weight of the thermoplastic elastomer is more than 800 parts by weight, shape retention of the adhesive layer becomes difficult. On the other hand, when the content of the non-volatile hydrocarbon oil is not more than 50 parts by weight, the adhesive becomes too hard and sufficient skin adhesiveness tends to be unachieved. Particularly, the followability to the moving skin during adhesion becomes poor, sometimes resulting in falling off during application. From such aspect, the content of the non-volatile hydrocarbon oil in the adhesive layer is preferably 51 parts by weight-800 parts by weight, more preferably 60 parts by weight-600 parts by weight, most preferably 70 parts by weight-500 parts by weight, relative to 100 parts by weight of the thermoplastic elastomer.

The content of the non-volatile hydrocarbon oil in the adhesive layer is preferably 23.5 wt %-88 wt %, more preferably 25 wt %-85 wt %, most preferably 26.5 wt %-83 wt %.

When a "thermoplastic elastomer" and a "non-volatile hydrocarbon oil" are applied to the drug storage layer, as regards the thermoplastic elastomer and the non-volatile hydrocarbon oil, the non-volatile hydrocarbon oil is preferably used at a proportion of 10-1200 parts by weight, more preferably 50-800 parts by weight, relative to 100 parts by weight of the thermoplastic elastomer.

The drug storage layer may further contain one or more kinds selected from the group consisting of alcohol solvents, amide solvents, ester solvents, liquid organic acids, carboxylic acid salts, lactone and surfactants to enhance dispersibility and transdermal absorbability of rivastigmine in the drug storage layer.

The contents of the alcohol solvent, amide solvent, ester solvent, liquid organic acid, carboxylic acid salt, lactone, and surfactant in each preferable embodiment and drug storage layer are the same as those in the "adhesive layer maintaining the drug" in the patch of the aforementioned first embodiment.

Good skin adhesiveness can be exhibited by containing a thermoplastic elastomer and a non-volatile hydrocarbon oil at the above-mentioned contents and content ratio. The adhesive layer may contain a tackifier as necessary.

The "tackifier" here is the same as the "tackifier" of the "adhesive layer maintaining the drug" of the patch of the aforementioned first embodiment, and preferable embodiments thereof are also the same. The content of the tackifier in the adhesive layer is not more than 10 wt % in embodiment 1. The content is preferably not more than 5 wt %, more preferably not more than 2 wt %, further preferably not more than 1 wt %, and the absence of a tackifier is most preferable. In relation to the skin adhesiveness of the adhesive skin patch, the content of the tackifier is prepared according to the kind, content and content ratio of the thermoplastic elastomer and non-volatile hydrocarbon oil.

The drug storage layer and the adhesive layer in the patch of the second embodiment may contain, as optional components, pharmaceutically conventional additives such as excipient, dispersing agent, stabilizer, viscous agent, antioxidant, softening agent, flavoring agent, colorant and the like, as long as the characteristics of the present invention are not impaired. Preferably embodiments of each additive are the same as those of the patch of the aforementioned first embodiment.

The patch of the second embodiment is prepared by spreading a drug storage layer and an adhesive layer having the above-mentioned constitutions on a support. The "support" here is the same as the "support" of the patch of the aforementioned first embodiment, and preferable embodiments thereof are also the same.

The patch of the second embodiment can also be provided with a release liner conventionally used in the field of patch. The "release liner" here is the same as the "release liner" of the patch of the aforementioned first embodiment, and preferable embodiments thereof are also the same.

In the patch of the second embodiment, the drug storage layer can be obtained by, for example, dissolving a drug and a polymer in a solvent and applying and drying same on a support, or applying and drying same on a release liner to form a drug storage layer on the surface of the release liner, and thereafter adhering the support by pressing same on the drug storage layer. The adhesive layer can be produced by dissolving each of a thermoplastic elastomer and a drug or a salt thereof in a non-volatile hydrocarbon oil, dissolving or dispersing same in a solvent such as toluene and the like to prepare a coating liquid for forming an adhesive layer, applying the obtained coating liquid on the above-mentioned drug storage layer or release liner, and then drying same. When an adhesive layer is formed on a release liner, a patch can be obtained by press adhering same to the drug storage layer. A coating liquid for forming a drug storage layer and an adhesive layer can be applied using, for example, a conventionally-used coater such as roll coater, die coater, gravure roll coater, reverse roll coater, kiss-roll coater, dip roll coater, bar coater, knife coater, spray coater and the like.

poration were dissolved in 230 parts by weight of toluene per 100 parts by weight of the mixture. To the aforementioned solution were added liquid paraffin ("KAYDOL", "Hydrobrite 550PO", "Hydrobrite HV" manufactured by Sonneborn Limited) and rivastigmine and the mixture was mixed and stirred to give a coating liquid for forming an adhesive layer.

The above-mentioned coating liquid was applied to a silicone-treated poly(ethylene terephthalate) (PET) film (release liner) such that the rivastigmine content of the adhesive layer after drying was 1.8 mg/cm$^2$. After drying in an oven at 80° C. for 1 hr, a PET film (support) was laminated on the surface of the adhesive layer, which was cut in a 15 cm×30 cm size to give the object patch. In the Table, SIS/SI ratio is a weight ratio.

TABLE 1

| component | | | | Ex. 1 | Ex. 2 | Ex. 3 | Ex. 4 | Ex. 5 | Ex. 6 | Ex. 7 | Ex. 8 | Ex. 9 | Ex. 10 |
|---|---|---|---|---|---|---|---|---|---|---|---|---|---|
| thermoplastic elastomer | styrene-isoprene-styrene block copolymer (SIS)/styrene-isoprene block copolymer (SI) mixture | product name D1119 5505 5229 | SIS/SI ratio 34/66 50/50 80/20 | 30 | 30 | | 30 | 57 | 47.5 | 38 | 28.5 | 25 30 | 21 9 |
| non-volatile hydrocarbon oil | liquid paraffin | product name KAYDOL Hydrobrite 550PO Hydrobrite HV | viscosity *$^2$ mm$^2$/s 67 97 247 | 63 | 62.95 | 56 | 38 | 47.5 | 57 | 66.5 | 70 | 65 | 65 |
| non-volatile hydrocarbon oil content (parts by weight/thermoplastic elastomer 100 parts by weight) | | | | 210 | 210 | 187 | 67 | 100 | 150 | 233 | 280 | 217 | 217 |
| antioxidant | | tocopherol | | | | 0.05 | | | | | | | |
| rivastigmine | | | | 7 | 7 | 14 | 5 | 5 | 5 | 5 | 5 | 5 | 5 |

*$^1$; Numerical values in Table show content (wt %) in adhesive layer.
*$^2$; measured at 40° C.

In addition, the aforementioned solution is preferably dried under heating at, for example, about 40° C.-150° C. The adhesive layer after drying, which contains the drug, is preferably 10 g/m$^2$-1,000 g/m$^2$, more preferably 20 g/m$^2$-800 g/m$^2$.

EXAMPLES

The present invention is explained in more detail in the following by referring to Examples and Comparative Examples, which are not to be construed as limitative.

Examples 1-10

Preparation of Patch Containing Rivastigmine

According to the formulation shown in Table 1, each component constituting the adhesive layer was weighed. First, a styrene-isoprene-styrene block copolymer (SIS)/styrene-isoprene block copolymer (SI) mixture ("KRAYTON D1119" manufactured by Kraton Performance Polymers Inc.) (weight average molecular weight: 207,500), and "JSR SIS5505", "JSR SIS5229" manufactured by JSR Cor- Comparative Example 1

In the formulation of Example 1 in Table 1, a commercially available heat-curable pressure-sensitive acrylic adhesive ("Duro tak 87-2194", manufactured by Henkel Japan Ltd., solid content=40 wt %) was weighed instead of the styrene-isoprene-styrene block copolymer/styrene-isoprene block copolymer mixture, such that the solid content was the same as the thermoplastic elastomer content in Table 1, and liquid paraffin was added. Rivastigmine was dissolved and added, and the mixture was stirred to give a coating liquid for forming an adhesive layer.

The coating liquid was applied on a silicone-treated PET film (release liner), prepared such that the weight of the adhesive layer after drying was 100 g/m$^2$ and dried in an oven at 80° C. for 60 min. However, the liquid was not hardened and a patch could not be obtained.

Comparative Examples 2, 3

According to the formulations shown in Table 2, each component constituting the adhesive layer was measured, and a patch was prepared in the same manner as in Example 1. As for Comparative Example 2, sufficient adhesiveness was not obtained and, as for Comparative Example 3, the adhesive layer could not be maintained and evaluation was not possible.

TABLE 2

| component | | product name | SIS/SI ratio | Com. Ex. 2 | Com. Ex. 3 |
|---|---|---|---|---|---|
| thermo-plastic elastomer | styrene-isoprene-styrene block co-polymer (SIS)/ styrene-isoprene block copolymer (SI) mixture | D1119 5505 5229 | 34/66 50/50 80/20 | 70 | 10 |
| | | product name | viscosity *2 mm²/s | | |
| non-volatile hydrocarbon oil | liquid paraffin | KAYDOL Hydrobrite 550PO Hydrobrite HV | 67 97 247 | 25 | 25 |
| non-volatile hydrocarbon oil content (parts by weight/ thermoplastic elastomer 100 parts by weight) | | | | 36 | 850 |
| antioxidant | tocopherol | | | | |
| rivastigmine | | | | 5 | 5 |

*1; Numerical values in Table show content (wt %) in adhesive layer.
*2 measured at 40° C.

A: no protrusion of adhesive layer even when compressed

B: almost no protrusion of adhesive layer even when compressed

C: on compression, adhesive layer is deformed and protrudes from support but is restored after release of compression D: on compression, adhesive layer is deformed and protrudes from support and is not restored easily even after release of compression <Degree of Detachment in Bathing>

The patches prepared in the Examples and Comparative Examples were punched out in a circular shape with a diameter of 36 mm, adhered to the chest of five healthy volunteers, and the degree of detachment in bathing was evaluated according to the following criteria.

A: no detachment in 5 volunteers

B: end portion was detached in 1-2 volunteers but did not fall off

C: patch fell off in 1-2 volunteers

D: fell off in 3 or more volunteers

The measurement results of the above-mentioned adhesive property tests are shown in Table 3.

TABLE 3

| property | Ex. 1 | Ex. 2 | Ex. 3 | Ex. 4 | Ex. 5 | Ex. 6 | Ex. 7 | Ex. 8 | Ex. 9 | Ex. 10 |
|---|---|---|---|---|---|---|---|---|---|---|
| peel strength (N/25 mm) | 1.07 | 1.16 | 3.63 | 4.38 | 4.65 | 3.63 | 2.29 | 3.38 | 2.74 | 2.82 |
| ball tackiness | 24 | 26 | 20 | 32 or more | 32 or more | 30 | 32 or more | 32 or more | 30 | 26 |
| adhesion (mm) | — | — | — | 4 | 0 | 8 | 5 | 2 | 50 | 50 |
| protrusion | B | B | C | A | A | B | C | D | B | A |
| detachment in bathing | C | C | D | D | D | B | B | A | B | C |

Experimental Example 1

Adhesive Property Tests

<Peel Strength>
A patch cut in 25 mm×300 mm was adhered to a stainless (SUS304) plate, and a stress on detachment in the 180° direction at a speed of 300 mm/min was measured.
<Ball Tackiness>
A ¹/₃₂ inch-1 inch ball was rolled, after a 100-mm approach, down on an inclined plane with an angle of inclination of 30°, onto which a patch cut in 100 mm width was adhered, and the nominal diameter of the largest ball that stopped on the patch for not less than 5 seconds was measured.
<Holding Force>
A patch cut in 25 mm×300 mm was adhered to a stainless (SUS304) plate, a 25 g load was hung in the 90° direction for 60 min, and the detached distance was measured.
<Protrusion>
The end portion of the patches prepared in the Examples and Comparative Examples was compressed with a finger from the top of the support, and the level of protrusion was evaluated according to the following criteria.

From Table 3, it was clarified that each patch of the Examples of the present invention showed appropriate detachment strength, and sufficient tackiness. When highly viscous liquid paraffin was used, each patch was superior in peel strength and holding force, and by controlling the liquid paraffin content, a preparation with less protrusion of the adhesive layer and less detachment in bathing was obtained.

Experimental Example 2

In Vitro Skin Permeability Test

According to the method described in WO 2006/093139, the skin extracted from the abdomen of a male Wister rat (5-week-old) was set on a vertical Franz diffusion cell. Commercially available rivastigmine-containing patches (rivastigmine content=1.8 mg/cm²) wherein a drug layer and an adhesive layer are formed on each patch and each support of Examples 1-3 were each punched out in a circular shape with area 1.0 cm² to give samples, which were adhered to the rat skin on the diffusion cell (n=3). On the receptor side, the content of rivastigmine in the receptor solution was measured over time by high performance liquid chromatography (HPLC) using 10% by volume ethanol saline. The measurement conditions of HPLC are shown below.

<HPLC Measurement Conditions>

HPLC system: high performance liquid chromatograph (LC2010C) manufactured by SHIMADZU CORPORATION column: ODS, 4.6 mmφ×15 cm, 5 μm
column temperature: 25° C.
mobile phase: buffer/methanol=50/50
(buffer; 5.0 mM sodium 1-heptane sulfonate, 1% by volume phosphoric acid)
detection wavelength: 220 nm
flow: 0.8 mL/min In the above-mentioned skin permeability test, the amount of rivastigmine that permeated the rat skin was determined 24 hr after adhesion of the sample and shown in Table 4.

TABLE 4

| patch | amount of rivastigmine that permeated skin 24 hr after adhesion of sample (μg/cm$^2$) |
|---|---|
| Example 1 | 521 |
| Example 2 | 554 |
| Example 3 | 728 |
| Example 4 | 370 |
| Example 5 | 385 |
| Example 6 | 400 |
| Example 7 | 410 |
| Example 8 | 410 |
| Example 9 | 365 |
| Example 10 | 355 |
| commercially available rivastigmine-containing patch | 360 |

From Table 4, it was shown that the amount of each patch of Examples 1-3 of the present invention was higher than that of the commercially available rivastigmine-containing patch having the same rivastigmine content per unit area, and almost equivalent to that in Examples 4-10, thus showing good skin permeability of the present invention.

Experimental Example 3

Primary Skin Stimulation Test

Three days before the start of adhesion, dorsal hair of kbs:JW female domestic rabbit (17-week-old) was shaven with an electric clipper, and the patch of Example 1 and a commercially available rivastigmine-containing patch which were each cut into a 2.5 cm square were adhered to the skin (n=3). Oil paper was placed thereon to cover the adhesion site, an underlap tape (manufactured by Nichiban Co., Ltd.) was wound from the chest to the whole abdomen, and a jacket for domestic rabbit (BJ03, manufactured by Bioresearch Center Co., Ltd.) was set thereon. After fixing for 24 hr, the sample was removed, and the level of skin irritation reaction was evaluated based on the method described in J. Pharmacol. Exp. Ther. 82, 377-390 (1944) at 1 hr, 24 hr, 48 hr and 72 hr after the removal.

That is, at each of the above-mentioned times, erythema and eschar formation and edema formation were evaluated according to the following evaluation criteria, and scored. An average of respective evaluation points was determined, the primary evaluation value was calculated, and an average of the average evaluation value at each of the above-mentioned times was determined for each domestic rabbit and taken as a primary irritation index (P.I.I.). The P.I.I. value was 0 at the lowest and 8 at the highest, and the values are divided into 4 categories of primary skin irritation reaction shown in Table 5.

<Evaluation Criteria of Skin Irritation Reaction>

[Formation of Erythema and Escahr]

no erythema; 0 score
very slight (barely perceptible level of) erythema; 1 score
well-defined erythema; 2 scores
moderate to severe erythema; 3 scores
severe erythema to eschar formation of level preventing erythema scoring; 4 scores

[Formation of Edema]

no edema; 0 point
very slight (barely perceptible level of) edema; 1 score
slight edema (edges of area well defined by definite raising); 2 scores
moderate edema (raised approximately 1 mm); 3 scores
severe edema (raised more than 1 mm and extending beyond exposure area); 4 scores

TABLE 5

| category of skin primary stimulation reaction | P.I.I. |
|---|---|
| no stimulation | 0-0.4 |
| weak stimulation | 0.5-1.9 |
| moderate stimulation | 2-4.9 |
| strong stimulation | 5-8 |

The results of the skin primary stimulation test are shown in Table 6.

TABLE 6

| | P.I.I |
|---|---|
| Example 2 | 0 |
| Example 5 | 0 |
| Example 8 | 0 |
| Example 9 | 0 |
| Example 10 | 0 |
| commercially available rivastigmine-containing patch | 2.92 |

From Table 6, the commercially available rivastigmine-containing patch showed P.I.I. value of 2.92, thus showing the moderate level stimulation. In contrast, the patches of the Examples showed P.I.I. value of 0 and were evaluated to have no stimulation, thus showing low skin irritation.

Experimental Example 4

Stability Test

The preparations obtained in Examples 1 and 9 were sealed in the same packing material as the commercially available rivastigmine preparation, and preserved together with the commercially available rivastigmine preparation at 40° C., 75% RH. The adhesive layer of the preparation in the initial and after preservation (1 month and 3 months later) was dissolved in THF, the rivastigmine content was quantified by HPLC, and the drug residual ratio after preservation to that at the initial was compared.

The measurement results of the above-mentioned stability test are shown in Table 7.

TABLE 7

| property | Ex. 1 | Ex. 9 | commercially available rivastigmine-containing patch |
|---|---|---|---|
| drug residual ratio (wt %) 1 month later | 99.1 | 98.6 | 99.1 |
| drug residual ratio (wt %) 3 months later | — | 99.2 | 97.2 |

From Table 7, Examples 1 and 9 of the present invention showed about the same level of stability as the commercially available rivastigmine patch.

Example 11

Preparation of Patch Containing Rivastigmine

According to the formulation shown in Table 8, each component constituting the drug storage layer was weighed. First, a styrene-isoprene-styrene block copolymer (SIS)/styrene-isoprene block copolymer (SI) mixture ("KRAYTON D1119" manufactured by Kraton Performance Polymers Inc.) (weight average molecular weight: 207,500) was dissolved in 230 parts by weight of toluene per 100 parts by weight of the mixture. To the aforementioned solution were added liquid paraffin ("Hydrobrite HV" manufactured by Sonneborn Limited) and rivastigmine and the mixture was mixed and stirred to give a coating liquid for forming a drug storage layer.

The above-mentioned coating liquid was applied to a silicone-treated poly(ethylene terephthalate) (PET) film (release liner) such that the rivastigmine content of the drug storage layer after drying was 1.8 mg/cm². After drying in an oven at 80° C. for 1 hr, a PET film (support) was laminated on the surface of the drug storage layer to give the object drug storage layer.

On the other hand, according to the formulation shown in Table 8, each component constituting the adhesive layer was weighed. First, a styrene-isoprene-styrene block copolymer (SIS)/styrene-isoprene block copolymer (SI) mixture ("KRAYTON D1119" manufactured by Kraton Performance Polymers Inc.) (weight average molecular weight: 207,500) was dissolved in 230 parts by weight of toluene per 100 parts by weight of the mixture. To the aforementioned solution was added liquid paraffin ("Hydrobrite HV" manufactured by Sonneborn Limited) and the mixture was mixed and stirred to give a coating liquid for forming an adhesive layer.

The above-mentioned coating liquid was applied to a silicone-treated poly(ethylene terephthalate) (PET) film (release liner) such that the weight of the adhesive layer after drying was 100 mg/cm². After drying in an oven at 80° C. for 1 hr, a drug storage layer was laminated on the surface of the adhesive layer, which was cut in a 15 cm×30 cm size to give the object patch.

TABLE 8

| component | | drug storage layer | adhesive layer |
|---|---|---|---|
| thermoplastic elastomer | styrene-isoprene-styrene block copolymer (SIS)/styrene-isoprene block copolymer (SI) mixture | 28.5 | 30 |
| non-volatile hydrocarbon oil | liquid paraffin | 66.5 | 70 |
| rivastigmine | | 5 | — |

*1; Numerical values in Table show content (wt %) in drug storage layer and adhesive layer.

The patch of Example 11 was subjected to the aforementioned Experimental Example 2 (in vitro skin permeability test), and the amount of rivastigmine that permeated the rat skin was determined 24 hr after adhesion of the sample and shown in Table 9.

TABLE 9

| patch | amount of rivastigmine that permeated skin 24 hr after adhesion of sample (µg/cm²) |
|---|---|
| Example 1 | 380 |
| commercially available rivastigmine-containing patch | 360 |

From Table 9, it was shown that the amount of the patch of Example 1 of the present invention was almost equivalent to that of the commercially available rivastigmine-containing patch, thus showing good skin permeability.

The patch of Example 11 was subjected to the aforementioned Experimental Example 3 (skin primary stimulation test), and the skin irritation was evaluated. The results are shown in Table 10.

TABLE 10

| | P.I.I |
|---|---|
| Example 11 | 0 |
| commercially available rivastigmine-containing patch | 2.92 |

From Table 10, the commercially available rivastigmine-containing patch showed P.I.I. value of 2.92, thus showing the moderate level stimulation. In contrast, the patch of the Example 11 showed P.I.I. value of 0 and was evaluated to have no stimulation, thus showing low skin irritation.

INDUSTRIAL APPLICABILITY

As described in detail above, the present invention can provide a patch of rivastigmine having sufficient skin adhesiveness and low skin irritation, showing good skin permeability of rivastigmine, and sufficient transdermal absorbability.

This application is based on patent application Nos. 2012-133268, 2012-230286, 2012-230287, 2012-230284 and 2012-230285 filed in Japan, the contents of which are incorporated in full herein.

The invention claimed is:

1. A patch comprising an adhesive layer maintaining a drug, which is formed on a support, wherein the adhesive layer comprises a thermoplastic elastomer,
    liquid paraffin in an amount exceeding 50 parts by weight and not more than 800 parts by weight per 100 parts by weight of the elastomer, and rivastigmine or a salt thereof, wherein the adhesive layer is free of a tackifier, a content of liquid paraffin in the adhesive layer is not less than 35 wt %, the liquid paraffin has a kinematic viscosity at 40° C. of not less than 80 mm$^2$/s, and the thermoplastic elastomer is a styrene-based block copolymer that is a mixture of a styrene-isoprene-styrene (SIS) block copolymer and a styrene-isoprene (SI) block copolymer with a SIS block copolymer to SI block copolymer weight ratio of 10/90 to 82/18.

2. The patch according to claim 1, wherein a content of the liquid paraffin in the adhesive layer is not more than 88 wt %.

3. The patch according to claim 1, wherein a content of the liquid paraffin in the adhesive layer is more than 150 parts by weight and not more than 250 parts by weight per 100 parts by weight of the thermoplastic elastomer.

4. The patch according to claim 2, wherein a content of the liquid paraffin in the adhesive layer is not less than 50 wt % and not more than 70 wt %.

5. The patch according to claim 1, wherein the adhesive layer is free of an antioxidant.

6. The patch according to claim 2, wherein a content of the liquid paraffin in the adhesive layer is more than 150 parts by weight and not more than 250 parts by weight per 100 parts by weight of the thermoplastic elastomer.

7. The patch according to claim 6, wherein a content of the liquid paraffin in the adhesive layer is not less than 50 wt % and not more than 70 wt %.

\* \* \* \* \*